United States Patent [19]
Coenen et al.

[11] Patent Number: 5,500,118
[45] Date of Patent: Mar. 19, 1996

[54] BIOGAS REACTOR FOR THE ANAEROBIC TREATMENT OF WASTE WATER

[75] Inventors: Hubert Coenen, Aarbergen; Helmut Hubert, Wiesbaden; Michael Zumbragel, Aarbergen, all of Germany

[73] Assignee: Passavant-Werke AG, Germany

[21] Appl. No.: 261,907

[22] Filed: Jun. 15, 1994

[30] Foreign Application Priority Data

Jun. 17, 1993 [DE] Germany .......................... 43 20 096.6

[51] Int. Cl.⁶ .................................................. C02F 3/28
[52] U.S. Cl. ......................... 210/603; 210/188; 210/218
[58] Field of Search ................................... 210/188, 218, 210/539, 603

[56] References Cited

U.S. PATENT DOCUMENTS

| | | | |
|---|---|---|---|
| 4,166,791 | 9/1979 | Marvin | 210/188 |
| 4,391,704 | 7/1983 | Anderson | 210/188 |
| 4,622,147 | 11/1986 | Vellinga | 210/539 |
| 4,940,546 | 7/1990 | Vogelpohl | 210/188 |

FOREIGN PATENT DOCUMENTS

| | | |
|---|---|---|
| 0244029 | 10/1989 | European Pat. Off. . |
| 454803 | 12/1927 | Germany . |
| 2904449 | 8/1979 | Germany . |
| 2728585 | 8/1979 | Germany . |
| 3327775 | 2/1985 | Germany . |
| 4201864 | 7/1993 | Germany . |
| 62-279891 | 12/1987 | Japan . |

*Primary Examiner*—Christopher Upton
*Attorney, Agent, or Firm*—Larson and Taylor

[57] ABSTRACT

In UASB-type biogas reactors, the biogas is separated from the rising waste water stream by collection hoods arranged in staggered fashion, in which a zero pressure level is maintained, at which the gas transition takes place. In cross-section shapes of existing collection hoods, the zero pressure surface is sharply reduced when the water level is high, and the conversion to gas is correspondingly sharply reduced. Therefore, in accordance with the invention, a rectangular section shape is employed in which the zero pressure surface remains unchanged. The topside of the collection hoods can be formed as a smooth sliding surface in the shape of a roof for the anaerobic sludge sediment.

9 Claims, 1 Drawing Sheet

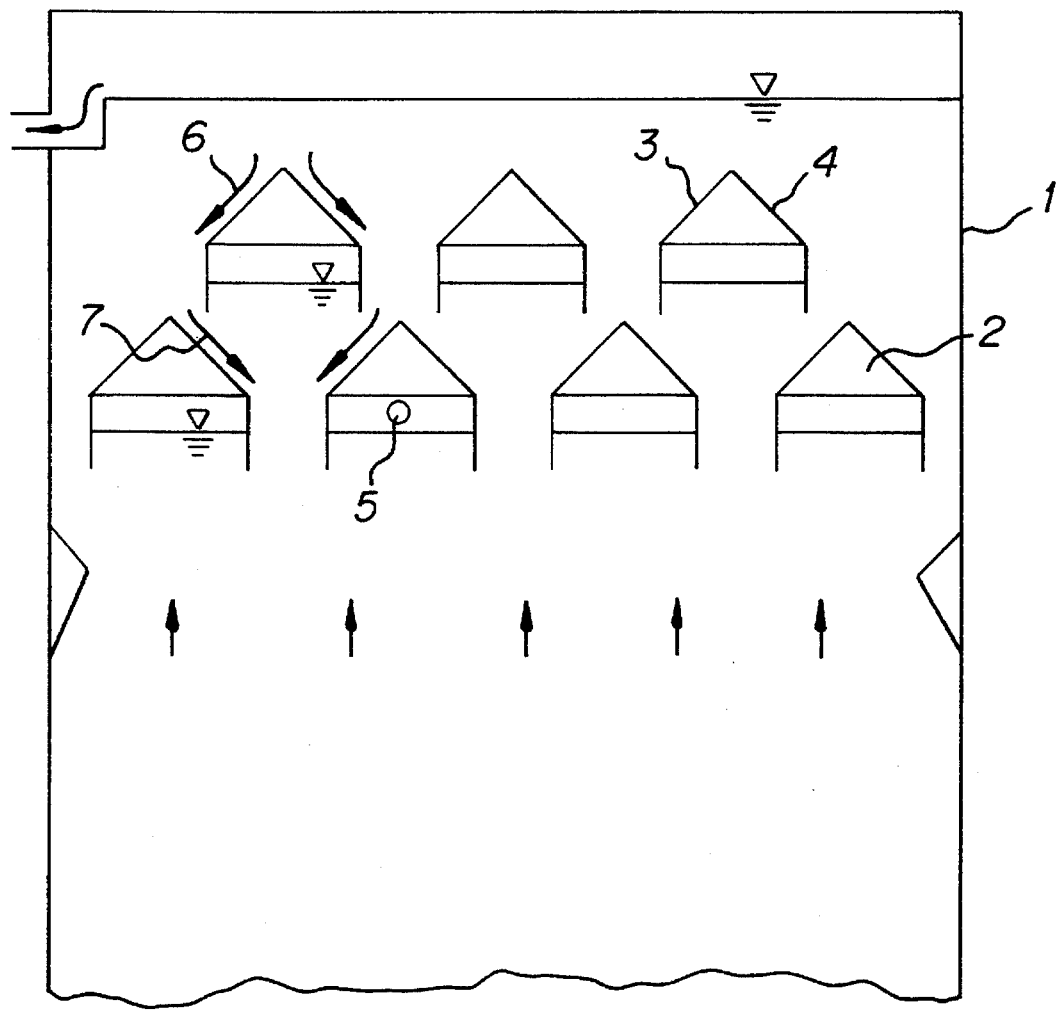

BIOGAS REACTOR FOR THE ANAEROBIC TREATMENT OF WASTE WATER

FIELD OF THE INVENTION

The invention relates to biogas reactors for the anaerobic treatment of waste water in the well-known process called "UPFLOW." The biogas reactors operating in the upcurrent possess, in their upper portion, at least one biogas collection hood, in which, driven by gas counterpressure, a liquid level is built up and maintained. The collection hoods have the vertical cross-section of an inverted funnel (DE-A 27 28 585). Semi-tubular cross-sections are also found (I)E-A-42 01 864).

BACKGROUND OF THE INVENTION

Cross-sections of existing collection hoods have the disadvantage that the size of the interface between gas and liquid constantly changes with oscillation of the liquid level. In case of a high liquid level, the release of gas from the liquid is strongly hindered because of the reduced surfaces. In the extreme case, as a remit of high turbulence, this can lead to overflow of the biomass into the gas chamber. Another undesired effect is the tendency toward foam production.

SUMMARY OF THE INVENTION

The task of overcoming these disadvantages is solved according to the invention in that the collection hood, at least in the region of liquid level oscillation, has a horizontal cross-section that remains constant. Furthermore, the upper side of the collection hood can be provided with sloping surfaces that enable the biosludge to slip off. The phase interface for the gas transition thus remains constant for all elevations of the liquid level. The sliding surfaces for the sludge, placed as a roof on the topside of the collection hoods, can be used for absorbing bending and shear forces.

BRIEF DESCRIPTION OF THE DRAWING

The Figure shows a vertical section through a biogas reactor.

DESCRIPTION OF THE PREFERRED EMBODIMENTS

A biogas reactor 1 includes collection hoods 2, that are staggered in two overlapping planes. The collection hoods have a downward-open U-cross-section with sharp corners upon which the two sloping surfaces 3, 4 are placed in the form of a roof. Exhaust 5 for the collected biogases lies, preferably, on the front face of the exhaust hoods. The sludge still contained in the upward-flowing waste water settles in the weak flow areas above the collection hoods, on the oblique sliding surfaces, and slides along the path of arrows 6 and 7 back down into the sludge bed.

We claim:

1. A biogas reactor for anaerobic treatment of waste water, said biogas reactor including a collection hood comprising:
    a lower portion for holding waste water;
    an upper portion for holding biogas formed during biological decomposition of the waste water;
    a roof defining a top end of said upper portion;
    means for maintaining an oscillation region between said upper portion and said lower portion during operation of said biogas reactor, said oscillation region comprising a phase-transition interface having a constant horizontal cross-sectional area; and
    submerging means for keeping said collection hood completely submerged in said waste water stream during operation of said biogas reactor.

2. The biogas reactor according to claim 1 wherein said roof comprises two sloping surfaces having opposite inclinations for allowing biosludge to slide off during operation of said biogas reactor.

3. The biogas reactor according to claim 1 wherein said roof comprises two sloping surfaces having opposite inclinations for absorbing flexion and transverse forces.

4. The biogas reactor according to claim 1 wherein the horizontal cross-sectional area of said oscillation region comprises a rectangular shape.

5. The biogas reactor according to claim 1 comprising at least two collection hoods staggered in two overlapping planes.

6. The biogas reactor according to claim 1 wherein said collection hood further comprises an exhaust for collecting the biogas.

7. The biogas reactor according to claim 6 wherein said exhaust is positioned on a front face of said collection hood.

8. The biogas reactor according to claim 1 wherein walls of said oscillation region are parallel.

9. A method for anaerobically treating waste water using a biogas reactor comprising a collection hood having a lower portion for holding waste water, an upper portion for holding biogas formed during biological decomposition of the waste water and a roof defining a top end of the upper portion, said method comprising:
    completely submerging said collection hood in the waste water stream and maintaining an oscillation region between the upper and lower portion of the collection hood during biological decomposition of the waste water, said oscillation region comprising a phase-transition interface having a constant horizontal cross-sectional area.

* * * * *